United States Patent
Wang et al.

(12) 
(10) Patent No.: US 6,323,021 B1
(45) Date of Patent: Nov. 27, 2001

(54) MUTANT STRAIN OF PENICILLIUM CITRINUM AND USE THEREOF FOR PREPARATION OF COMPACTIN

(75) Inventors: Yun-Ping Wang; Yen-Chun Chen; Weimao Chang; Chi-Luan Lin, all of Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 09/334,739

(22) Filed: Jun. 17, 1999

(30) Foreign Application Priority Data

Jan. 15, 1999 (TW) ............................................ 88100591 A

(51) Int. Cl.⁷ .............................. C12N 1/14; C12P 17/06
(52) U.S. Cl. ...................... 435/254.5; 435/125; 435/441
(58) Field of Search ..................................... 435/119, 125, 435/441, 254.5

(56) References Cited

U.S. PATENT DOCUMENTS

| | | | |
|---|---|---|---|
| 3,983,140 | * 9/1976 | Endo | 424/279 |
| 4,231,938 | 11/1980 | Monaghan et al. | 260/343.5 |
| 5,362,638 | 11/1994 | Dahiya | 435/125 |
| 5,409,820 | 4/1995 | Gerson et al. | 435/125 |

* cited by examiner

*Primary Examiner*—Irene Marx
(74) *Attorney, Agent, or Firm*—Fei-Fei Chao; Venable, Baetjer, Howard & Civiletti

(57) ABSTRACT

A novel microorganism, *Penicillium citrinum* CCRC 930024 and a process of using the microorganism for the production of compactin comprising cultivating *Penicillium citrinum* CCRC 930024 in a fermentation medium and recovering compactin from the fermentation broth are disclosed.

12 Claims, 2 Drawing Sheets

MUTANT STRAIN OF PENICILLIUM CITRINUM AND USE THEREOF FOR PREPARATION OF COMPACTIN

BACKGROUND OF THE INVENTION

1. Field of the Invention

The present invention relates to a novel microorganism and uses thereof in preparation of antihypercholesterolemic agents. More specifically, it relates to a mutant strain of *Penicillium citrinum* ATCC 38065, and its use in preparation of compactin.

2. Description of the Related Arts

High blood cholesterol levels are recognized as being one of the main causes of cardiopathy, e.g. cardiac infarction, arteriosclerosis or hyperlipaemia. Cholesterol biosynthesis is greatly reduced by inhibiting the activity of 3-hydroxy-3-methylglutaryl-coenzyme A (HMG-CoA) reductase, which is a rate controlling enzyme. As a result, considerable research has been undertaken with a view to discover physiologically acceptable substances which are capable of inhibiting cholesterol biosynthesis and thus are capable of reducing blood cholesterol levels.

Many antihypercholesterolemic agents are presently used to cure cardiopathy disease and one of the best-known antihypercholesterolemic agents is pravastatin, which is prepared from modifying compactin, the only precursor of pravastatin. Thus, a process that can prepare compactin at a high concentration level is urgently required.

Compactin was first purified from the nutrient medium of *Penicillium brevicocompactum* and found to be an antifugal metabolite, as disclosed by Brown et al in 1975. Later, Endo et al in Japan Sankyo Company found that compactin exists in the fermentation broth of *Penicillium citrinum*. They also discovered compactin has blood cholesterol reducing ability.

U.S. Pat. No. 3,983,140 (Sep. 28, 1976) and U.S. Pat. No. 4,049,495 (Sep. 20, 1977) patented by A. Endo et al disclosed fermentative preparation of compactin by cultivation of a microorganism belonging to *Penicillium citrinum*.

U.S. Pat. No. 5,691,173 (Nov. 25, 1997) patented by Scott Primrose et al disclosed the preparation of compactin by fermentation using a microorganism belonging to *Penicillium adametzoides*.

In prior patents, compactin is prepared at an extremely low concentration level. Therefore, a novel microorganism or a new preparation is required to produce compactin at a high concentration level.

SUMMARY OF THE INVENTION

An object of the present invention is to provide a novel microorganism capable of producing compactin using fermentation.

An another object of the present invention is to provide a process of producing compactin using the novel microorganism.

According to one aspect of the present invention, a mutant strain *Penicillium citrinum* ATCC 38065, which is capable of secreting compactin, is deposited at the American Type Culture Collection (ATCC), 10801 University Blvd., Manassas, Va. 20110-2209, and is given an accession number of PTA-3429, before the issuance of the patent, under the provisions of the Budapest Treaty for the International Recognition of the Deposit of Microorganisms for the purpose of Patent Procedure. A viable sample of this mutant strain is currently deposited at the Food Industry Research Development Institute (FIRDI), R.O.C., under accession No. CCRC 930024.

According to another aspect of the invention, a process of preparing compactin using *Penicillium citrinum* CCRC 930024 which comprises cultivating *Penicillium citrinum* CCRC 930024 in a fermentation medium and recovering compactin from the fermentation broth is provided.

Preferably, before cultivation in the fermentation medium, *Penicillium citrinum* CCRC 930024 is cultivated in a spore medium to germinate spores and the spores are cultivated in a seed medium.

Other objects, features, and advantages of the present invention will become apparent from the following detailed description.

DETAILED DESCRIPTION OF THE INVENTION

The present invention is based on the observation that compactin is produced by a novel microorganism very different from that employed by prior patents. The novel microorganism is a mutant strain of *Penicillium citrinum* ATCC 38065. This mutant strain is capable of secreting compactin. A viable sample of this mutant strain is currently deposited at the Food Industry Research Development Institute (FIRDI), R.O.C., under accession No. CCRC 930024. A viable sample of this mutant strain (CCRC 930024) is deposited at the American Type Culture Collection (ATCC), 10801 University Blvd., Manassas, Va. 20110-2209, and is given an accession number of PTA-3429, before the issuance of the patent, under the provisions of the Budapest Treaty for the International Recognition of the Deposit of Microorganisms for the purpose of Patent Procedure.

*Penicillium citrinum* CCRC 930024 can be obtained by applying a conventional mutation-inducing technique to the parent strain, *Penicillium citrinum* ATCC 38065. For example, irradiation of the microorganisms with gamma rays or ultraviolet light, or treatment with a mutagen, such as N-methyl-N'-nitro-N-nitrosoguanidine, ethylmethane sulfonate and hydroxylamine are suitable methods of inducing mutation. Then mutant strains which are filipine-resistant can be selected and the desired mutant, *Penicillium citrinum* CCRC 930024, is obtained as a strain capable of producing compactin at the highest concentration level among all mutant strains.

In this embodiment, all microorganisms are cultivated by the same process for producing compactin at the highest concentration level, the process comprising the steps of: (a) germinating spores in a spore medium; (b) cultivating the spores in a seed medium; and (c) cultivating the seed culture in the fermentation medium. But for simplifying the production process, microorganisms can be directly cultivated in the fermentation medium to produce compactin.

The spore medium can be malt-extract-agar (MEA) medium or potato-dextrose-agar (PDA) medium. The MEA can be composed of malt extract, peptone, and agar. Preferably, MEA contains 2% of malt extract, 0.1% peptone, and 2% of agar. The PDA medium can contain potato extract, D(+)glucose, agar and glycerol. Preferably, the PDA medium contains 20% of potato extract, 2% of D(+)glucose, 2% of agar and 5–10% of glycerol.

Researchers found that the spore-producing ability was increased in proportion to the content of glycerol in the spore medium. Therefore, the spore-producing activity of the *Penicillium citrinum* CCRC 930024 can be increased, depending on the amount of glycerol in the spore medium.

The seed medium can contain glucose, glycerol, corn steep liquor and yeast power. Preferably, the seed medium contains 2% of glucose, 1% of glycerol, 2% of corn steep liquor, and 0.5% of yeast powder and has a pH about 4–9.

The fermentation medium can contain glucose, glycerol, pharmamedia®, soybean meal, corn steep liquor, $KH_2PO_4$, $K_2HPO_4$, $FeSO_4$ and $CaCO_3$. Preferably, the fermentation medium contains 7% of glucose, 3% of glycerol, 2% of pharmamedia®, 1% of soybean meal, 1% of corn steep liquor, 0.15% of $KH_2PO_4$, 0.05% of $K_2HPO_4$, 0.003% of $FeSO_4$ and 0.2% of $CaCO_3$ and has a pH about 4–7.

| MEA medium | | PDA medium | |
|---|---|---|---|
| Malt extract | 2% | Potato extract | 20% |
| Peptone | 0.1% | D(+) glucose | 20% |
| Agar | 2% | Agar | 2% |
| | | Glycerol | 1% |
| Seed medium | | Fermentation medium | |
| Glucose | 2% | Glucose | 7% |
| Glycerol | 1% | Glycerol | 3% |
| Corn steep liquor | 2% | Pharmamedia ® | 2% |
| Yeast powder | 0.5% | Soybean meal | 1% |
| | | Corn steep liquor | 1% |
| | | $KH_2PO_4$ | 0.15% |
| | | $K_2HPO_4$ | 0.05% |
| | | $FeSO_4$ | 0.003% |
| | | $CaCO_3$ | 0.2% |

Compactin titer in the fermentation broth is determined by HPLC under mobile conditions of 20% of methanol and 80% of water throughout a Merck RP-18 (254×4 mm) column. The Detection wavelength was 237nm. Compactin is identified by the retention time in comparison with a standard obtained from Sigma Company.

Without intending to limit it in any manner, the present invention will be further illustrated by the following examples.

Figure 1:
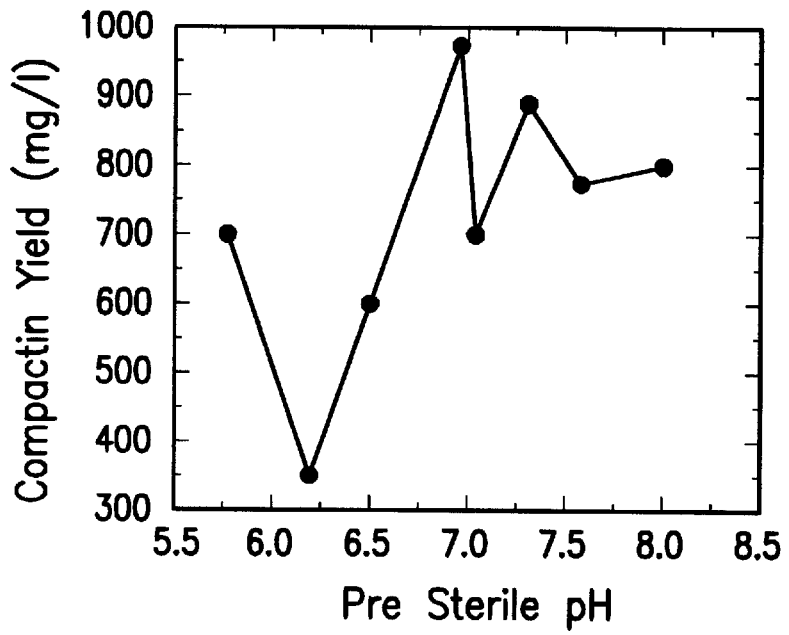
FIG. 1 is a diagram illustrating the influence of the pre-sterile pH of the fermentation medium (x-axis) on the compactin yield of *Penicillium citrinum* CCRC 930024 (y-axis).

EXAMPLE 1
Induction of *Penicillium citrinum* CCRC 930024

A culture of *Penicillium citrinum* ATCC 38065 was subjected to single spore isolation. After the isolation, 138 strains were obtained and it was found that 77 strains gave a compactin titer below 30 mg/L, 31 strains gave a compactin titer of 100 to 120 mg/L, and just one strain gave a compactin titer up to 220 mg/L. The results were itemized in the following Table 1.

TABLE 1

| Concentration level of compactin (mg/L) | 0 | 20 | 40 | 60 | 80 | 100 | 120 | 140 | 160 | 180 | 200 | 220 |
|---|---|---|---|---|---|---|---|---|---|---|---|---|
| Strain Number of *Penicillium citrinum* ATCC 38065 | 24 | 53 | 3 | 3 | 5 | 15 | 16 | 8 | 6 | 1 | 3 | 1 |

The strain having the highest compactin titer, about 220 mg/L, was selected and cultivated on malt extract agar (MEA) at 25° C. for 7–10 days. The spore suspension was eluted from MEA by using 0.5 M potassium phosphate buffer with pH 7.0. The spore suspension was centrifuged twice. Then, the collected spores were mutagenized physically, e.g. by irradiating with gamma rays or UV light at a distance of 35 to 40 cm for 2.5 mins, or chemically, e.g. by treating with NTG, ethyl methane sulfonate or hydroxyamine at a concentration of 1 mg/ml for 1 hour. Then the mutated spores were cultivated at 25° C. for 5 to 7 days on MEA further containing filipine at a concentration of 5 μg/ml. Here, filipine belongs to polyene antibiotics. As a result, 144 filipine-resistant mutants were selected and were cultivated to determine their compactin titer. It was found that 70 strains gave a compactin titer below 300 mg/L and 16 strains gave a compactin titer up to 1500 to 1800 mg/L, as indicated in the following Table 2.

TABLE 2

| Concentration level of compactin (× 100 mg/L) | 0–3 | 3–6 | 6–9 | 9–12 | 12–15 | 15–18 |
|---|---|---|---|---|---|---|
| Number of mutated *Penicillium citrinum* ATCC 38065 | 70 | 14 | 4 | 14 | 26 | 16 |

One of 16 mutant strains having a compactin titer up to 1500 to 1800 mg/L was found to be stable and to produce compactin at a concentration level extremely higher than those found in prior art. The mutant strain was deposited at the Food Industry Research Development Institute (FIRDI), R.O.C. under accession No. CCRC 930024. A viable sample of this mutant strain is deposited at the American Type Culture Collection (ATCC), 10801 University Blvd., Manassas, Va. 20110-2209, and is given an accession number of PTA-3429, before the issuance of the patent, under the provisions of the Budapest Treaty for the International Recognition of the Deposit of Microorganisms for the purpose of Patent Procedure.

Experiments were initiated in a pre-culture stage to germinate spores of *Penicillium citrinum* CCRC 930024 in a spore medium.

A culture of *Penicillium citrinum* CCRC 930024 was inoculated on potato-dextrose-agar (PDA) and incubated at 25° C. for 7 to 10 days. The spores of *Penicillium citrinum* CCRC 930024 were eluted and centrifuged twice using physiological saline containing 1% Tween 80. Spore suspension was stored at 4° C. until ready to use. Production of compactin by using *Penicillium citrinum* CCRC 930024

The spore suspension of *Penicillium citrinum* CCRC 930024 was inoculated in the seed medium and shaken at 25–30° C. for 2 days. The seed medium was obtained by mixing 2% of glucose, 1% of glycerol, 2% of corn sheep liquor and 0.5% of yeast power, adjusting the pH to 4–9 using HCl or NaOH before sterilization and sterilizing the mixture at 121° C. for 20 mins.

The seed culture of *Penicillium citrinum* CCRC 930024 was inoculated into a 500 ml flask containing 50 ml of fermentation medium at 10% inoculum size, and shaken at 25 to 30° C. for 5 days. The fermentation medium was obtained by mixing 7% of glucose, 3% of glycerol, 2% of pharmarmedium, 1% of soybean meal, 1% of corn steep liquor, 0.15% of $KH_2PO_4$, 0.05% of $K_2HPO_4$, 0.003% of $FeSO_4$, 0.2% OF $CaCO_3$ adjusting pH to 4–9 before sterilization using HCl or NaOH and sterilizing the mixture at 121° C. for 20 mins.

Then the fermentation broth was submitted for HPLC determination of compactin concentration. It was found that, under these conditions, *Penicillium citrinum* CCRC 930024 produced compactin at a concentration level of 1–1.5 g/L, much higher than the levels of the prior art.

EXAMPLE 2

The influence of the pre-sterile pH of the fermentation medium on the compactin-production level of *Penicillium citrinum* CCRC 930024 was studied. The same compactin-production procedure as described in Example 1 was employed except that the pre-sterile pH of fermentation medium was changed, the results were indicated in FIG. 1. It was found that the pre-sterile pH of fermentation medium has no influence on the compactin titer of *Penicillium citrinum* CCRC 930024 in a range of 6.8 to 8.0.

EXAMPLE 3

Figure 2:
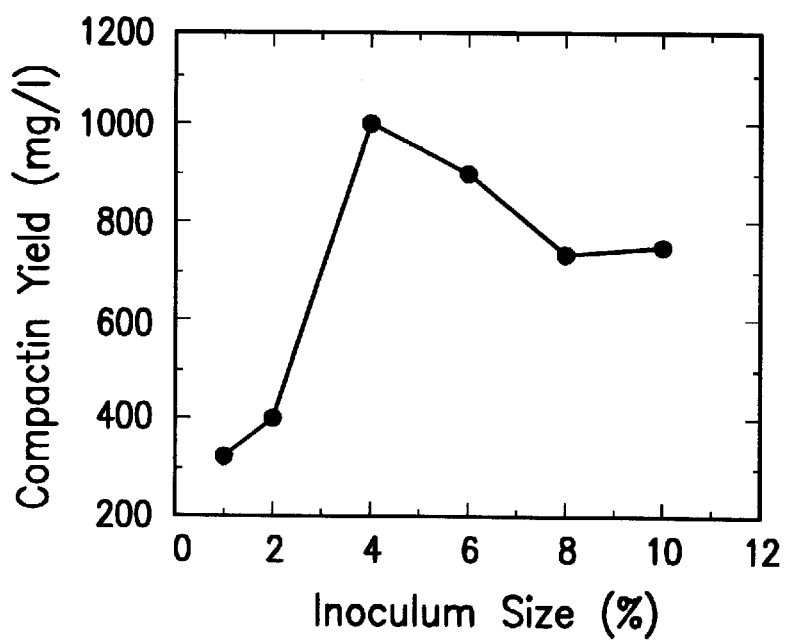
FIG. 2 is a diagram illustrating the influence of the inoculum size (x-axis) on the compactin yield (y-axis), when *Penicillium citrinum* CCRC 930024 was inoculated on the fermentation medium.

When *Penicillium citrinum* CCRC 930024 was inoculated on the fermentation medium, the influence of the inoculum size on its compactin titer was studied. The same compactin-production procedures as described in example 1 were employed except that the inoculum size was changed, the results were indicated in FIG. 2. Biosynthesis of compactin was high when the inoculum size was between 4–10%.

EXAMPLE 4

Because the metabolic rate of carbon is higher than that of nitrogen in the compactin biosynthesis, the C/N ratio of fermentation medium should be maintain at a constant range in order to obtain a high compactin titer.

Figure 3:
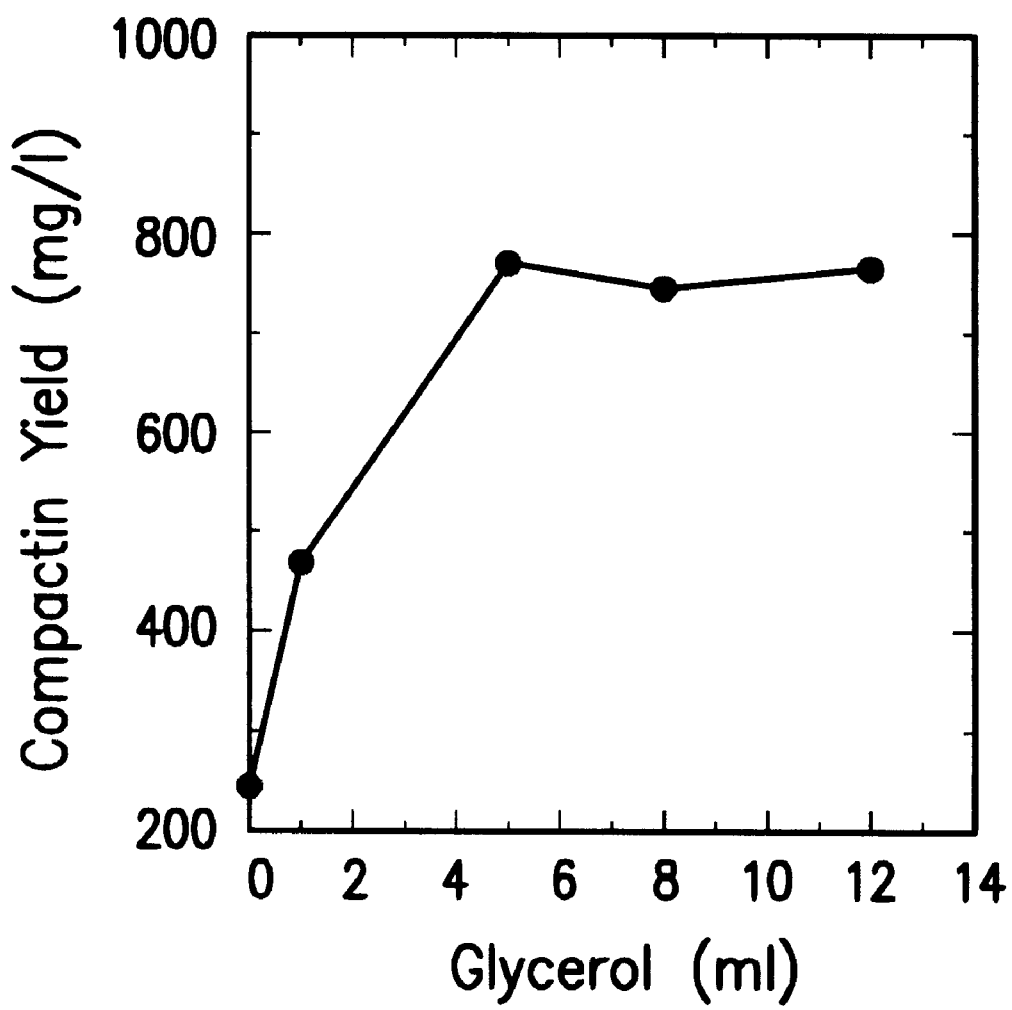
FIG. 3 is a diagram illustrating the amount of glycerol in the fermentation medium (x-axis) on the compactin yield of *Penicillium citrinum* CCRC 930024 (y-axis).

Thereby, the influence of the concentration of the carbon source in the fermentation medium on the compactin biosynthesis was also studied. The same compactin-production procedures as described in Example 1 were repeated except 1 ml, 4 ml, 8 ml and 12 ml of 50%(v/v) glycerol was added as the carbon source respectively into the fermentation medium after *Penicillium citrinum* CCRC 930024 was cultivated in the fermentation medium for 2 days. The results were indicated in FIG. 3. Compactin titer was increased in accordance with glycerol and reached the maximal level when the addition of glycerol was 4 ml, and wasn't changed when the addition of glycerol was higher than 4 ml.

As a result, after fermenting a period of time, adding suitable amount of glycerol into the fermentation medium can increase the compactin titer of *Penicillium citrinum* CCRC 930024.

EXAMPLE 5

The influence of the spore stability of *Penicillium citrinum* CCRC 930024 on the compactin titer was studied. After washing from the spore medium, the spores of *Penicillium citrinum* CCRC 930024 were stored at 4° C. for 0 day, 60 days, 120 days, 180 days, 270 days, and 360 days, respectively. Then the spores were cultivated in the same procedure as described in Example 1, respectively. The compactin titers were determined by HPLC and indicated in the following Table 3. The spores of *Penicillium citrinum* CCRC 930024 were found to have good stability.

TABLE 3

| Storing day | 0 | 60 | 120 | 180 | 270 | 360 |
|---|---|---|---|---|---|---|
| Compactin titer (mg/L) | 1532 | 1496 | 1528 | 1335 | 1162 | 987 |

While the invention has been particularly shown and described with the reference to the preferred embodiment thereof, it will be understood by those skilled in the art that various changes in form and details may be made without departing from the spirit and scope of the invention.

What is claimed is:

1. A mutant strain of *Penicillium citrinum* ATCC 38065, which is ATCC accession No. PTA-3429, wherein said mutant strain produces more than 1500 mg/L of compactin.

2. The mutant strain according to claim 1, wherein said compactin of said mutant strain is collected by cultivating said mutant strain in a fermentation medium and recovering said compactin from the fermentation broth.

3. The mutant strain according to claim 2, wherein said fermentation medium is presterilized at pH in a range of 3 to 9.

4. The mutant strain according to claim 2, wherein said mutant strain is cultivated at a temperature of 20 to 35° C.

5. The mutant strain according to claim 2, wherein said mutant is pre-cultivated in a spore medium and then in a seed medium before cultivating in said fermentation medium.

6. The mutant strain according to claim 5, wherein said spore medium is composed of potato extract, D(+) glucose, agar, and glycerol.

7. The mutant strain according to claim 5, wherein said seed medium is composed of glycerol, glucose, corn steep liquor and yeast powder.

8. The mutant strain according to claim 7, wherein said seed medium is pre-sterilized at pH in a range of 4 to 9.

9. The mutant strain according to claim 5, wherein said pre-cultivation in said spore medium is carried out at a temperature of 20 to 35° C.

10. The mutant strain according to claim 1, wherein said mutant strain was mutated by treating said *Penicillium citrinum* ATCC 38065 with a mutagen.

11. The mutant strain according to claim 10, wherein said mutant strain is further selected by filipine.

12. The mutant strain according to claim 1, wherein said mutant strain produces 1500 to 1800 mg/L of compactin.

* * * * *